United States Patent [19]

Madate et al.

[11] Patent Number: 4,572,627
[45] Date of Patent: Feb. 25, 1986

[54] EYE FUNDUS CAMERA

[75] Inventors: Haruhisa Madate, Kawasaki; Isao Matsumura, Yokosuka; Kyoji Sekiguchi, Tokyo, all of Japan

[73] Assignee: Canon Kabushiki Kaisha, Tokyo, Japan

[21] Appl. No.: 441,785

[22] Filed: Nov. 15, 1982

[30] Foreign Application Priority Data

Nov. 21, 1981 [JP] Japan .................. 56-187618
Nov. 21, 1981 [JP] Japan .................. 56-187619

[51] Int. Cl.⁴ .............................................. A61B 3/14
[52] U.S. Cl. .................................................. 351/206
[58] Field of Search ................ 351/206, 207, 208; 354/62

[56] References Cited

U.S. PATENT DOCUMENTS 4,149,787  4/1979  Kobayashi et al. ............. 351/206
4,283,124  8/1981  Matsumura ..................... 351/206

Primary Examiner—Rodney B. Bovernick
Attorney, Agent, or Firm—Fitzpatrick, Cella, Harper & Scinto

[57] ABSTRACT

An eye fundus camera comprising a photographing system for taking a picture of an eye fundus, a fundus illumination system for alternatively providing infrared light and visible light to illuminate the fundus, a viewer connected to the photographing system for the observation of the fundus, an image pick-up part containing therein an image pick-up tube and connected to the photographing system through a stationary wavelength dividing mirror which reflects infrared light and transmits visible light, and a light intercepting screen plate retractably disposed in the optical light path between the wavelength dividing mirror and the image pick-up tube.

15 Claims, 5 Drawing Figures

EYE FUNDUS CAMERA

BACKGROUND OF THE INVENTION

1. Field of the Invention

The present invention relates to an eye fundus camera and especially to a "non-mydriatic type" eye fundus camera for examining and taking a picture of the fundus of an eye to be examined without application of any mydriatic agent to the eye.

2. Description of the Prior Art

In the "non-mydriatic" type eye fundus camera in which infrared light is used for positioning for fundus observation and visible light is used for taking a picture of the fundus there is provided means for separating the light reflected from the fundus into two beam fluxes one of which is directed to the photographing film and the other toward TV observation system. As such separation means, a total reflection swing-up mirror has conventionally been used. However, to change over the photo-taking light beam of relatively large diameter requires a large swing-up mirror, so that the mechanism becomes complicated and bulky.

It has been proposed to use a dichroic mirror disposed obliquely to reflect infrared light but transmit visible light (U.S. Pat. No. 4,283,124). However, the manufacture of a high performance dichroic mirror is difficult and costly. It needs a large amount of labour and a long time. Practically the light separation performance of the dichroic mirror is not perfect, and usually several percents of reflected light or transmitted light still remain. Because of it, when the photo-taking light is directed to the film, a portion of the light also enters TV image pick-up tube at the same time, which causes undesirable phenomenons such as image flow on the TV monitor and sticking on the image pick-up tube.

Apart from the above-mentioned problems, there is another problem related to the visual-line-fixing lamp of the fundus camera.

As is well known in the art, the visual-line-fixing lamp is used to guide the line of vision in a determined direction. In the case of a "mydriatic type" eye fundus camera, an external visual-line-fixing lamp is conventionally used for this purpose. In examining one of the eyes of a patient, the other eye is looking at the lamp. In this case, since the pupil of the eye to be examined has previously been diluted with a mydriatic agent, there is never produced such a problem that the examination of the eye is disturbed by miosis caused by any "near reflex" of the eye. In contrast, in the case of the non-mydriatic eye fundus camera where a picture-taking of the eye fundus is carried out without the aid of a mydriatic agent, there is a possibility that the examination is disturbed by miosis caused by near reflex. For this reason, it is preferred to use an internal visual-line-fixing lamp for non-mydriatic type fundus camera (see U.S. Pat. No. 4,068,932). For an eye fundus camera which can be used as both the mydriatic type and non-mydriatic type, however, the use of an internal visual-line-fixing lamp brings forth a problem. That is, if a separate light guiding system is fixedly mounted in the camera in order to eliminate such a troublesome work of demounting the optical system for guiding light to the image pick-up tube by which an invisible image is transformed into a visible image and remounting it onto a direct view-finder, it is required to intercept any external light entering through the direct view-finder when a picture of the eye fundus is to be taken using the internal visual-line-fixing lamp and without mydriatic agent (when the camera is used in its non-mydriatic mode). Therefore the fundus camera is required to have a shutter or a light path change-over mechanism for changing over the light path from finder to lamp or vice versa. Obviously the provision of such an additional element renders the camera complicated in structure and large in size.

SUMMARY OF THE INVENTION

Accordingly it is an object of the invention to provide an eye fundus camera provided with a video camera, in which a mirror for selection for optical path to the video camera or the photosensitive film is fixed.

It is another object of the invention to provide an eye fundus camera which can be used as a non-mydriatic type fundus camera and also as an ordinary type fundus camera. When it is used as an ordinary type eye fundus camera, the examiner views the examined eye through a finder with a naked eye.

It is a further object of the invention to provide an eye fundus camera with which, when it is used as a non-mydriatic type camera, the person to be examined can perceive the visual-line-fixing object through the objective lens of the camera.

Other and further objects, features and advantages of the invention will appear more fully from the following description taken in connection with the accompanying drawings.

DESCRIPTION OF PREFERRED EMBODIMENTS

Figure 1:
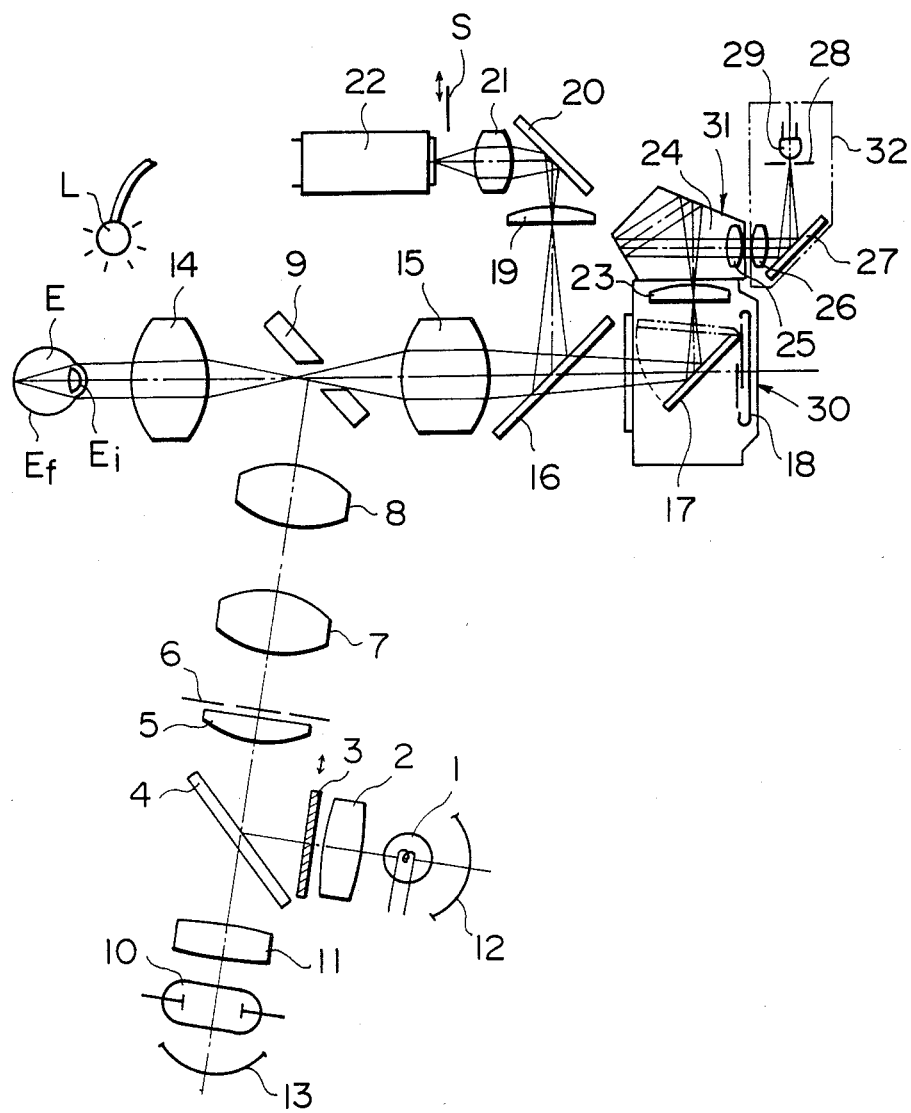
FIG. 1 is an optical sectional view showing an embodiment of the invention.

FIG. 1 shows the optical arrangement of an embodiment of the eye fundus camera according to the invention. In FIG. 1, the camera is shown as a non-mydriatic type camera in which infrared light is used to observe an eye E to be examined and visible light is used to take a picture of the fundus of the eye E.

Figure 2:
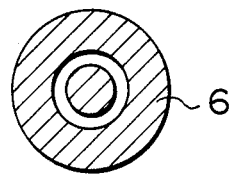
FIG. 2 is a plan view showing an element of the embodiment.
Figure 3:
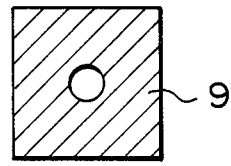
FIG. 3 is a plan view showing another element of the embodiment.
Figure 4:
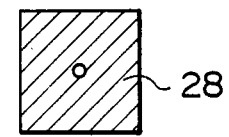
FIG. 4 is a plan view showing a further element of the embodiment.

Designated by 1 is a tungsten lamp serving as a light source for observation. The light emitted from the tungsten lamp 1 enters a dichroic mirror 4 through a condenser lens 2 and a filter 3 for cutting off the visible range light. The dichroic mirror 4 reflects infrared light, transmits a portion of visible light and also reflects a portion of visible light. The light deflected by the dichroic mirror 4 enters a perforated mirror 9 after passing through condenser lens 5, ring slit plate 6 and relay lenses 7 and 8 in the named order. A plan view of the ring slit plate 6 is shown in FIG. 2 and that of the perforated mirror 9 is shown in FIG. 3.

A photographing flash tube 10 (strobo tube) is disposed behind the dichroic mirror 4. The light emitted from the strobo tube 10 is projected on the dichroic mirror 4 through a condenser lens 11. The flash light transmitted through the dichroic mirror 4 enters the perforated mirror 9 along the optical path as that for the light from the tungsten lamp 1 described above. A reflector 12 is provided behind the tungsten lamp 1 to concentrate and reflect the light from the lamp. Similarly, a reflector 13 is provided behind the strobo tube 10.

The light incident on the perforated mirror 9 through the above illumination optical system is reflected toward the eye E by the perforated mirror 9 to illuminate the fundus Ef of the eye E. The light reflected from the eye fundus Ef goes back to the perforated mirror 9 and then enters an observation optical system. Between the eye E and the perforated mirror 9, there is disposed an objective lens 14. On the other side of the perforated mirror 9 and along the optical axis there are arranged a taking lens 15, a dichroic mirror 16, a swing-up mirror 17 and a photographing film 18 in the named order. The dichroic mirror 16 functions as an optical path divider and reflects infrared light while transmitting visible light. The light reflected by the dichroic mirror 16 enters a field lens 19 disposed at substantially conjugated position with the film 18. After passing through the field lens 19, the light is deflected by a reflecting mirror 20 to an image pick-up tube 22 through an image-forming lens 21. The image pick-up tube is sensitive mainly to infrared light. Instead of the image pick-up tube, there may be used a two-dimensional photo-detector array.

A retractable screen plate S is provided in front of the image pick-up tube 22 to prevent the light from entering the image pick-up tube when the film 18 is exposed to light for picture-taking.

On the reflection side of the swing-up mirror 17, there are provided a field lens 23, a penta-prism 24, a direct view-finder 25, an image-forming lens 26, a reflecting mirror 27, a visual-line-fixing chart 28 and a visible light emitting diode 29 arranged along the optical axis in the named order. The field lens 23 is conjugate with the above-mentioned film 18 and with the field lens 19. The optical path is deflected by the penta-prism 24 and also by the mirror 27. The visual-line-fixing chart 28 can be handled from the outside and moved in a horizontal plane. The chart 28 is illuminated by the light emitted from the visible light emitting diode 29.

In the illustrated embodiment, the mirror 17, field lens 23, penta-prism 24 and finder 25 are provided by using the body part 30 and finder part 31 of, for example, a single-lens reflex camera. On the other hand, the image-forming lens 26, reflecting mirror 27, visual-line-fixing chart 28 and light-emitting diode 29 are encased in a separate casing such as a visual line fixing lamp container 32. This container 30 is therefore formed as a unit attachable to the finder part 31 of the camera. L is an external visual-line-fixing lamp disposed out of the above optical path and can be put on when it is desired.

To observe the image on the monitor, the tungsten lamp 1 is put on. The light emitted from the tungsten lamp 1 together with the reflected light by the reflector 12 passes through the condenser lens 2. The light contains a visible light component and an infrared light component. The visible range cutting filter 3 filters out the visible light component from the light. The infrared light component transmitted through the filter is incident on the dichroic mirror 4. As the dichroic mirror has a particular property to reflect infrared light, the incident beam of infrared light is reflected by the dichroic mirror 4 toward the condenser lens 5 which forms an image of the light on the ring slit plate 6. The annular infrared beam passing through the ring slit plate 6 enters the perforated mirror 9 through the relay lenses 7 and 8. The infrared beam is reflected by the mirror 9 toward the objective lens 14. The objective lens 14 forms a light image of ring slit form near the iris Ei of the eye E. The beam of infrared light reflected from the fundus Ef and containing the fundus information enters again the objective lens 14 which forms an intermediate image of the fundus Ef. After passing through the center opening of the perforated mirror 9, the infrared beam is reflected by the dichroic mirror 16 and then forms an image of the fundus on the field lens 19 disposed at a substantially conjugate position with respect to the film 18. The infrared beam from the field lens 19 is reflected by the mirror 20 to the image-forming lens 21 which forms an image of the fundus Ef on the image pick-up tube 22. The fundus image projected on the image pick-up tube is converted into a visible image by conversion means such as a cathode ray tube, and the visible fundus image can be monitored.

When the camera is to be used as a non-mydriatic type eye fundus camera, the visual-line-fixing lamp container 32 is connected to the finder part 31 and then the light-emitting diode 29 is put on. The light emitted from the diode 29 illuminates the visual-line-fixing chart 28. An image of the chart 28 is formed in the vicinity of the field lens 23, conjugate with the film 18, through mirror 27, image-forming lens 26, direct view-finder 25 and penta-prism 24. The visual-line-fixing chart 28 is conjugate with the fundus Ef in respect to the total optical system after focusing is completed. Therefore, the light beam from the chart 28 is focused on the fundus Ef of the eye E through swing-up mirror 17, dichroic mirror 16, taking lens 15, perforated mirror 9 and objective lens 14. The person to be examined, therefore, can clearly look at the image of the chart 28 and the visual line is fixed in the direction of the chart image.

For taking a picture of the fundus of the eye E, the strobo tube 10 is flashed to expose the film 18. The visible light momentarily emitted from the strobo tube and transmitted through the dichroic mirror 4 goes along the same optical path as that of the above-described infrared beam for observation, and illuminates the fundus Ef. Since the swing-up mirror 17 is turned up to the broken-line position simultaneously with the light emission from the strobo tube 10, the light reflected from the fundus Ef goes under the swing-up mirror 17, after passing the dichroic mirror 16, and finally is projected on the film 18.

At the time of the above film exposure, there exists a small quantity of visible light reflected by the dichroic mirror 16 toward the field lens 19. If this visible light enters the image pick-up tube 22, it adversely affects the pick-up tube. To prevent this, the screen plate S is brought to the position to cover the incidence side surface of the image pick-up tube 22 when a film exposure is carried out. Thus, the screen plate S disposed in front of the image pick-up tube blocks the visible light against entering the image pick-up tube 22.

When the camera is used as a "mydriatic type" fundus camera, the visible range cut-off filter 3 is removed. Also, the visual-line-fixing lamp container 32 including the light-emitting diode 29 etc. is detached from the finder part 31. Instead, the external visual-line-fixing lamp L is put on. After guiding the patient's visual line to the lamp L, the examiner observes the fundus Ef through the finder 25 with naked eye, under illumination by visible light. The operation for film exposure in this case is entirely the same as that in the case of non-mydriatic type.

In the illustrated embodiment, the visible light emitting diode 29 is used as the light source of the internal visual-line-fixing lamp. However, a tungsten lamp also may be used for it. Further, it is also possible to guide the light from the tungsten lamp 1 provided for the observation of the fundus by means of a light guide or the like. In order to accord the movement of the internal visual-line-fixing lamp with the direction of movement of the eye E guided to the internal visual-line-fixing lamp, the light path may be deflected several times between the finder 25 and the visual-line-fixing chart 28 by use of reflection mirrors or the like.

Figure 5:
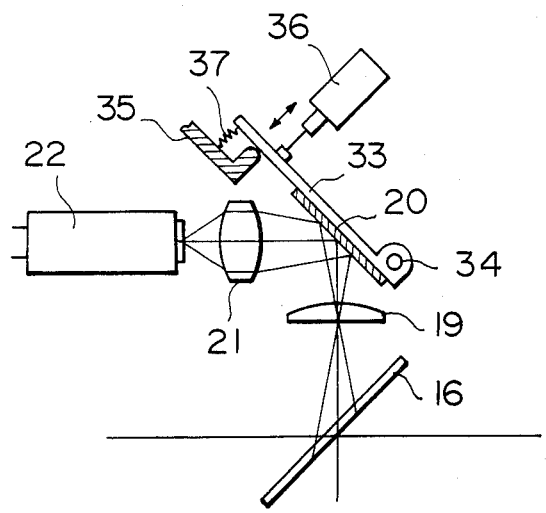
FIG. 5 is an optical sectional view showing the essential part of a modification of the embodiment.

FIG. 5 shows a modification of the above-described embodiment. In this modification, the reflection mirror 20 is bonded to a movable plate 33 to prevent the light from entering the image pick-up tube 22 at film exposure.

The movable plate 33 is pivotally supported by a shaft 34 for rotation about it. A stopper 35 determines the position of the mirror carrying plate 33 for guiding the light. One end of the plate 33 is connected to an electromagnetic solenoid 36 mounted on a stationary frame member, not shown. By the operation of the solenoid 36, the plate 33 is moved about the shaft 34 in the direction indicated by the arrow. Between the plate 30 and the stopper 35, a return spring 37 is disposed to return the plate 30 to the position abutting against the stopper 35 shown in FIG. 5.

During the time of fundus observation, the mirror carrying plate 33 is in the position shown in FIG. 5. The infrared reflected by the dichroic mirror 16 is guided to the image pick-up tube 22 by the reflection mirror 20. At the time of film exposure to take a picture of the fundus, the solenoid 36 is actuated to rotate the plate 33 about the pivot 34. In this rotated position, even if a small portion of the visible light is reflected by the dichroic mirror 16, the mirror 20 on the plate 33 deflects the visible light in other directions than the direction toward the image pick-up tube. In this case, since the deflection angle of light doubles the displacement angle of reflection mirror 20, the displacement of the mirror 20 required for preventing the visible angle from entering the image pick-up tube 22 is small. This makes it possible to reduce the size of the apparatus and shorten the response time.

While the invention has been particularly shown and described with reference to preferred embodiments thereof, it will be understood by those skilled in the art that the foregoing and other changes in form and details can be made therein without departing from the spirit and scope of the invention.

We claim:

1. An eye fundus camera comprising:
   a photographing system having a photo-taking light path for taking a picture of the fundus of an eye to be examined;
   a fundus illumination system for providing visible light and invisible light to illuminate said eye fundus;
   light dividing means fixedly disposed in said photo-taking light path for at least partially separating visible light and invisible light from each other by transmission and reflection;
   image receiving means optically associated with said photographing system through said light dividing means for receiving a visible light image of said eye fundus;
   invisible-light-responsive image pick-up means optically associated with said photographing system through said light dividing means to pick up an image of the eye fundus and produce an electrical signal; and
   means disposed relative to said image pick-up means for preventing the incidence of both said visible light and said invisible light, provided by said fundus illumination system, onto said image pick-up means from said light dividing means for a determined time period.

2. An eye fundus camera according to claim 1, wherein said light dividing means comprises a wavelength dividing mirror which reflects infrared light and transmits visible light.

3. An eye fundus camera according to claim 1, wherein said preventing means comprises a screen plate retractably inserted into said photo-taking light path.

4. An eye fundus camera according to claim 3, wherein said screen plate is inserted into said photo-taking light path when photo-taking is carried out.

5. An eye fundus camera according to claim 1, wherein said preventing means comprises a swing-mirror.

6. An eye fundus camera according to claim 1, further comprising a viewer connected to said photo-graphing system for the observation of said eye fundus with a naked eye.

7. An eye fundus camera according to claim 1, further comprising:
   a viewer connected to said photographing system for the observation of said eye fundus with a naked eye; and
   means attachable to said viewer to guide the visual line of said eye to be examined.

8. An eye fundus camera according to claim 7, wherein said visual line guiding means comprises a light source having a limited emitted light region and movable in a plane, and a relay optic.

9. An ophthalmological instrument comprising:
   a photographing system having an objective optical system opposed to an eye to be examined and optical image recording means disposed to receive an image formed by said objective optical system;
   an illumination system for providing illumination light to said eye and having an observation light source for emitting illumination light for observation and a picture-taking light source for emitting illumination light for picture-taking;
   wavelength dividing means;
   a viewer optically associated with said photographing system through said wavelength dividing means for receiving an illumination-light-for-picture-taking image of the fundus of said eye for observation thereof with a naked eye;
   image pick-up means, responsive to illumination light for observation and optically associated with said photographing system through said wavelength dividing means for receiving said illumination light for observation and picking up an image of said eye fundus and producing an electric signal; and
   means disposed relative to said image pick-up means for preventing image pick-up by said image pick-up means when said illumination light for picture taking is emitted from said picture-taking light source.

10. An instrument according to claim 9, further comprising means attachable to said viewer to guide the visual line of said eye to be examined.

11. An instrument according to claim 10, wherein said visual line guiding means comprises a light source having a limited emitted light region and movable in a plane, and a relay optic.

12. An instrument according to claim 9, wherein said illumination system includes wavelength selection means for selecting an infrared component in the light emitted from said picture-taking light source.

13. An instrument according to claim 12, wherein said wavelength selection means comprises a detachable filter disposed before said observation light source.

14. An instrument according to claim 9, wherein said preventing means comprises a shutter retractably disposed in the optical light path between said wavelength dividing means and said image pick-up means.

15. An instrument according to claim 10, wherein said preventing means comprises a mirror disposed to direct the light from said wavelength dividing means toward said image pick-up means, said mirror being mounted swingably.

* * * * *

UNITED STATES PATENT AND TRADEMARK OFFICE
CERTIFICATE OF CORRECTION

PATENT NO. : 4,572,627
DATED : February 25, 1986
INVENTOR(S) : Madate et al.

It is certified that error appears in the above-identified patent and that said Letters Patent is hereby corrected as shown below:

Column 1, line 35, change "phenomenons" to --phenomena--; and
         line 67, change "view-finder" to --viewfinder--.

Column 3, line 33, change "penta-prism" to --pentaprism--;
         line 34, change "view-finder" to --viewfinder--;
         line 36, change "light emitting" to --light-emitting--;
         line 43, change "light emitting" to --light-emitting--;
         line 45, change "penta-prism" to --pentaprism--; and
         line 50, change "visual line fixing" to --visual-line-fixing--.

Column 4, line 27-28, change "view-finder 25/and penta-prism" to --viewfinder 25 and pentaprism--.

Column 5, line 3-4, change "light emit-/ting" to --light-emitting--; and
         line 33, change "infrared reflected" to --infrared light reflected--.

Column 6, line 28, change "photo-graphing" to --photographing--.

Signed and Sealed this

Thirteenth Day of January, 1987

Attest:

DONALD J. QUIGG

Attesting Officer      Commissioner of Patents and Trademarks